United States Patent [19]

Omodei-Sale' et al.

[11] 4,370,337
[45] Jan. 25, 1983

[54] 1,2,4-TRIAZOLE DERIVATIVES AS ANTIFERTILITY AGENTS AND PHARMACEUTICAL COMPOSITIONS CONTAINING THEM

[75] Inventors: Amedeo Omodei-Sale', Voghera-Pavia; Pietro Consonni, Milan; Giulio Galliani, Monza, all of Italy

[73] Assignee: Gruppo Lepetit S.p.A., Milan, Italy

[21] Appl. No.: 283,715

[22] Filed: Jul. 16, 1980

Related U.S. Application Data

[62] Division of Ser. No. 87,376, Oct. 23, 1979.

[51] Int. Cl.$^3$ .................... A61K 31/41; C07D 249/08
[52] U.S. Cl. .................................. 424/269; 542/419; 548/262
[58] Field of Search .................. 548/262; 424/269

[56] References Cited

U.S. PATENT DOCUMENTS 4,119,635  10/1978  Omodei-Sale et al. ............ 548/262

FOREIGN PATENT DOCUMENTS 1351430  5/1974  United Kingdom ............... 548/262

*Primary Examiner*—Alton D. Rollins

[57] ABSTRACT

Novel 1,2,4-triazole derivatives are described having the following formula

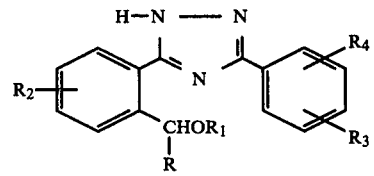

wherein R represents hydrogen or methyl, $R_1$ stands for hydrogen or ($C_1$–$C_4$)alkyl, or R and $R_1$ taken together may represent a further bond between the carbon atom and the oxygen atom, $R_2$ and $R_4$, each independently, represent hydrogen, chloro, fluoro, bromo, ($C_1$–$C_4$)alkyl or ($C_1$–$C_4$)alkoxy, $R_3$ stands for ($C_1$–$C_4$)alkyl, ($C_1$–$C_4$)alkoxy, allyloxy, propargyloxy, trifluoromethyl, phenyl, chloro, fluoro, bromo or dimethylamino or $R_3$ and $R_4$ taken together may represent a methylenedioxy group.

Also described is a process for their manufacture. Use of the novel compounds as antireproductive agents and pharmaceutical compositions containing them as active ingredient are also claimed.

1 Claim, No Drawings

1,2,4-TRIAZOLE DERIVATIVES AS ANTIFERTILITY AGENTS AND PHARMACEUTICAL COMPOSITIONS CONTAINING THEM

CROSS-REFERENCE TO RELATED APPLICATION

This is a divisional, of application Ser. No. 087,376 pending filed Oct. 23, 1979.

The present invention relates to a new class of 1,2,4-triazoles with antifertility activity, to the process for their preparation, to their use as antireproductive agents and to pharmaceutical compositions containing them. The new 1,2,4-triazoles of the present invention have the following general formula

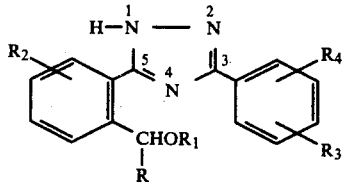

wherein R represents hydrogen or methyl, $R_1$ means hydrogen or $(C_1-C_4)$alkyl or R and $R_1$ taken together may represent a further bond between the carbon and the oxygen atom, $R_2$ represent hydrogen, chloro, fluoro, bromo, $(C_1-C_4)$alkyl or $(C_1-C_4)$alkoxy, $R_3$ stands for $(C_1-C_4)$alkyl, $(C_1-C_4)$alkoxy, allyloxy, propargyloxy, trifluoromethyl, phenyl, chloro, fluoro, bromo and dimethylamino and $R_4$ represents hydrogen, chloro, fluoro, bromo, $(C_1-C_4)$alkyl, or $(C_1-C_4)$alkoxy or $R_3$ and $R_4$ taken together may represent a methylenedioxy group.

As used herein the term "$(C_1-C_4)$alkyl" identifies a straight or branched alkyl radical having from 1 to 4 carbon atoms such as methyl, ethyl, propyl, 1-methylethyl, butyl, 1-methylpropyl, 2-methylpropyl and 1,1-dimethylethyl, and the expression "$(C_1-C_4)$alkoxy" identifies straight or branched alkoxy radicals having at most 4 carbon atoms selected from methoxy, ethoxy, propoxy, 1-methylethoxy, butoxy, 1-methylpropoxy, 2-methylpropoxy and 1,1-dimethylethoxy.

Other 5-(2-hydroxymethyl)phenyl-1H-1,2,4-triazoles and more particularly those bearing an unsubstituted or a nitro substituted phenyl group at the 3-position are described in Belgian Patent No. 786,562. Said patent covers a new class of 1-alkyl-3,5-disubstituted-1,2,4-triazoles having CNS depressant activity which can be prepared also by N-alkylating the corresponding 1-unsubstituted derivatives.

It will occur to any person skilled in the art that, owing to the great mobility of the hydrogen atom of 1,2,4-triazoles (see K. T. Potts, Chem. Rew., 61, 99, 1961 and, again, K. T. Potts. J. Chem. Soc. 3451, 1954) the compounds of the invention may also exist as the corresponding tautomeric forms

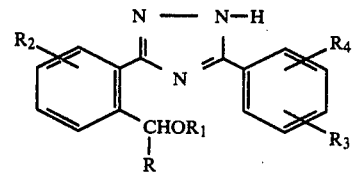

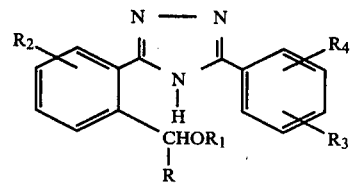

wherein the hydrogen atom is located on one of the other two nitrogen atoms of the triazole nucleus.

Since it is known that tautomeric forms rapidly exchange into each other, being in a state of dynamic equilibrium, it is intended that said tautomeric forms have to be considered as a part of the invention even though, throughout the specification the 3,5-disubstituted-1H-1,2,4-triazole derivatives of the present invention have been numbered according to formula I.

The compounds of the present invention possess remarkable antifertility and anti-reproductive properties. A second object of the present invention is a general method for preparing the novel 1,2,4-triazoles which comprises, as the first step, the preparation of the 2-hydroxymethyl derivatives, i.e. compounds of formula I wherein R and $R_1$ represent hydrogen, which can be synthesized by rearrangement of hydrazones of substituted benzaldehydes with 4-hydrazino-1H-2,3-benzoxazines of the formula

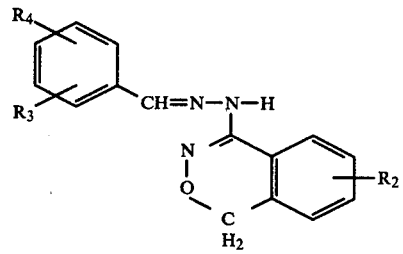

In the actual practice the rearrangement is carried out, according to J. Heterocycl. Chem. 9, 58 (1972), simply by refluxing the starting hydrazones in a high boiling inert organic solvent such as xylene, halogenated aromatic hydrocarbons, N,N-dimethylformamide and the like, for about 30 to 120 minutes and then recovering the final compounds by filtration.

Treatment of these 2-hydroxymethyl compounds with an oxidizing agent such as manganese dioxide, chromic acid, chromic anhydride and pyridine, lead tetraacetate or ceric salts affords the corresponding aldehydes. Compounds of formula I in which R represents methyl and $R_1$ is hydrogen are obtained by treating the corresponding derivatives in which R and $R_1$ taken together represent a further C—O bond with magnesium methyliodide in an inert organic solvent and then hydrolyzing the obtained organomagnesium compounds according to the well known Grignard reaction.

Finally compounds of formula I wherein independently from the meanings of R, $R_1$ represents an alkyl group are prepared from the corresponding alkohols by common etherification procedures.

As anticipated the 3,5-disubstituted-1,2,4-triazoles of the present invention possess a remarkable anti-reproductive activity.

More particularly, they show a very interesting post-coital-implantation antifertility activity when administered by different pharmacological routes, to laboratory animals, e.g. rats, hamsters, dogs, monkeys and baboons.

Moreover, the antifertility activity of these new compounds is not associated with other biological effects which are usual with hormonal substances. Fertility regulation can usually be achieved in a number of ways through the administration of hormonal substances. These can involve ovulation inhibition, ova transport, fertilization, implantation of the zygote, resorption of the fetus or abortion. Only with ovulation inhibition has there developed a successful method that is clinically useful.

The compounds of this invention allow an entirely new approach to this problem in which a non-hormonal compound can be administered parenterally, orally or by intravaginal route once or more times as needed after a "missed period" or to induce termination of a more advanced pregnancy.

Representative experiments for assessing antifertility activity were carried out with female Syrian golden hamsters weighing 100 to 130 g. The animals were mated and the presence of sperm in the vagina was taken as evidence of mating. The day sperm was detected was considered day one of pregnancy, since in our laboratory and those of other investigators 90 to 100% of animals that mate as evidenced by vaginal sperm are pregnant.

Pregnancy was later confirmed at the time of autopsy by presence of fetuses or implantation sites in the uterus.

Even if an animal aborts the fetus, implantation scars still remain as evidence that the animal has been pregnant.

The compounds of the invention, which possess a high solubility in the commonly employed pharmaceutical vehicles, were dissolved in sesame oil and administered subcutaneously in doses of 10 mg/kg daily for 5 days beginning on day 4 of pregnancy (days 4–8). The animals were autopsied on day 14 of pregnancy and the uteri were examined for evidence of pregnancy (implantation sites, fetal resorptions or live fetuses), hemorrage, and evidence of abnormalities of the uterus, placenta or fetuses. A compound was considered to be active if there was a reduction of live fetuses in at least 60% of the treated animals and the presence of implantation sites proves the animal to have been pregnant. In representative experiments the compounds of Examples 1 and 3 prove to be active according to the above mentioned criteria. The compounds were then studied for dose-activity relationships and the corresponding $ED_{50}$ values i.e., 100% activity (absence of live fetuses) in 50% of the animals, were also determined. The following table reports the $ED_{50}$ values of some representative compounds of the invention:

TABLE I

| Compound of Example | $ED_{50}$ mg/Kg s.c. hamsters |
|---|---|
| 1 | 0.08 |
| 3 | 0.1 |

Favorable results were also obtained by administering the compounds of the invention by oral route. The experiments for assessing this property were carried out on hamsters following the same procedure as above, with the obvious exception that the compounds were adminstered orally instead of subcutaneously.

The reduction of 60% of live fetuses was observed at an oral dosage of 20 mg/Kg with compounds of Examples 1 and 3. The $ED_{50}$ values were also determined and are reported in the following table:

TABLE II

| Compound of Example | $ED_{50}$ mg/Kg p.o. hamsters |
|---|---|
| 1 | 10 |
| 3 | >10>20 |

The compounds of the invention display a very low toxicity. In fact, their $LD_{50}$-values, determined according to Lichtfield and Wilcoxon, Journ. Pharm. Expt. Ther., 96, 99, 1949, are never lower than 600 mg/Kg, when administered to mice by intraperitoneal route.

The facts that the compounds of the invention possess an outstanding antireproductive activity even when administered by oral route and are very soluble in the common pharmaceutical carriers represent undoubtedly further important properties. As an example, the high solubility causes the compounds to be readily absorbable and incorporated into suitable and more tolerable injectable dosage forms which possess less drawbacks than corresponding forms wherein the active ingredient is suspended in the carrier. On the other hand, also the activity by oral route allows the compounds to be embodied into more acceptable pharmaceutical preparations. It is also to be noted that, apart from oral contraceptives which however are substances of steroidal nature and display their activity by blocking the ovulation, no other anti-reproductive compounds or preparations are known to be active per os.

A further object of the present invention is the use of the novel 1,2,4-triazole derivatives as antireproductive agents, with reference to all industrially applicable aspects and acts of said use, including the formulation of the novel compounds into pharmaceutical compositions.

For oral administration the substances are compounded in such forms as tablets, dispersible powders, capsules, granules, syrups, elixirs and solutions.

The compositions for oral use may contain one or more conventional adjuvants, such as, for instance, sweetening agents, flavoring agents, coloring agents, coating and preservative agents, in order to provide an elegant and palatable preparation. Tablets may contain the active ingredient admixed with conventional pharmaceutical acceptable excipients, e.g. inert diluents such as calcium carbonate, sodium carbonate, lactose and talc, granulating and disintegrating agents, such as, for instance, starch, alginic acid and sodium carboxymethylcellulose, binding agents, e.g. starch, gelatin, gum-arabic and polyvinylpyrrolidone and lubricating agents, e.g. magnesium stearate, stearic acid and talc. Syrups, elixirs and solutions are formulated as known in the art.

Together with the active compounds they may contain suspending agents, such as, for instance, methylcellulose, hydroxyethylcellulose, tragacanth and sodium alginate, wetting agents, e.g. lecithin, polyoxyethylene stearates and polyoxyethylene sorbitan monooleate and the common preservative, sweetening and buffering agents.

A capsule or a tablet may contain the active ingredient alone or admixed with an inert solid diluent, such as, for instance, calcium carbonate, calcium phosphate and kaolin.

Besides the oral route, other useful ways for administering the compounds of the invention may be suitably employed, such as, for instance, the subcutaneous or the intramuscular administration.

The active ingredient is thus embodied into injectable dosage forms. Such compositions are formulated according to the art and may contain appropriate dispersing or wetting agents and suspending or buffering agents identical or similar to those mentioned above.

Sesame oil, benzyl alcohol, benzyl benzoate, peanut oil and their mixtures may also be suitably employed as vehicles.

A vaginal insert may also contains the active ingredient in admixture with the common carriers e.g. gelatin, adipic acid, sodium bicarbonate, lactose and analogs. The compounds of the invention may also be administered in the form of their non toxic pharmaceutically acceptable acid addition salts. Such salts possess the same degree of activity as the free bases, from which they are readily prepared by reacting the base with an appropriate acid and accordingly, are included within the scope of the invention. Representative of such salts are the mineral acid salts, such as, for instance, the hydrochloride, hydrobromide, sulfate and the like and the organic acid salts such as the succinate, benzoate, acetate, p-toluenesulfonate, benzene sulfonate, maleate, tartrate, methanesulfonate, cyclohexylsulfonate and the like.

The dosage of active ingredient employed for inhibiting reproduction may vary within wide limits, depending on the nature of the compound.

Generally, good results are obtained when the compounds of the above formula I are administered in a single dosage from about 0.8 to about 50 mg/kg intramuscularly or in a multiple dosage (for from 5 to 10 days) of 1.0 to 50 mg/kg orally or intravaginally.

The dosage forms useful for this purpose generally contain from about 10 to about 600 mg of the active ingredient in admixture with a solid or liquid pharmaceutically acceptable carrier or diluent.

The following non limitative examples describe, in detail some representative compounds of this invention and the methods employed for their preparation.

EXAMPLE 1

5-(2-hydroxymethylphenyl)-3-(3-methoxyphenyl)-1H,-1,2,4-triazole

A suspension of 16 g of 4-[2-(3-methoxybenzyliden)-hydrazino]-1H-2,3-benzoxazine in 160 cc of anhydrous xylene is refluxed for 45 minutes and then, cooled in an ice bath. The solid which precipitates is recovered by filtration and recrystallized from ethanol yielding 14.7 g of the compound of the title, M.p. 157°-59° C.

EXAMPLE 2

3-(4-chlorophenyl)-5-(2-hydroxymethylphenyl)-1H-1,2,4-triazole

The compound of the title is prepared following the procedure described in the foregoing example starting from 4-[2-(4-chlorobenzyliden)hydrazino]-1H-2,3-benzoxazine. Yield 57%. M.p. 252°-54° C. (from ethanol).

EXAMPLE 3

2-[5-(3-methoxyphenyl)-1H-1,2,4-triazol-3yl]benzaldehyde 5 g of 5-(2-hydroxymethylphenyl)-3-(3-methoxyphenyl)-1H-1,2,4-triazole are added to a suspension of 25 g of manganese dioxide in 500 cc of anhydrous benzene and the mixture is stirred at room temperature for 6 hours. Then four portions of manganese dioxide, 5 g each, are added at intervals of one hour and, when the reaction, which is followed by thin layer chromtography, is completed, the mixture is filtered through celite. While the filtrate is concentrated to dryness yielding 0.78 g of the compound of the title, the residue is taken up with water and brought to pH 10 by means of 10% sodium hydroxide. After stirring at room temperature for 20 minutes the mixture is filtered again through celite and the filtrate is adjusted to pH 6 by addition of 8% hydrochloric acid. A precipitate forms which is recovered by filtration and dried yielding 3.34 g of the compound of the title. The two crops, 0.78 g plus 3.34 g, are gathered together and recrystallized from isopropyl ether/methylene chloride yielding 3 g of pure compound, M.p. 163°-65° C.

EXAMPLE 4

2-[5-(4-chlorophenyl)-1H-1,2,4-triazol-3-yl)]benzaldehyde

Following substantially the same procedure of the foregoing example and starting from the corresponding 3-(4-chlorophenyl)-5-(2-hydroxymethylphenyl)-1H-1,2,4-triazole, the compound of the title is obtained in 84% yield. M. p. 198°-200° C.

Typical compounds which can be prepared according to the procedures described in the above examples are as follows:
3-(3-ethoxyphenyl)-5-(2-hydroxymethylphenyl)-1H-1,2,4-triazole
3-(3-allyloxyphenyl)-5-(2-hydroxymethylphenyl)-1H-1,2,4-triazole
2-[5-(3-ethoxyphenyl)-1H-1,2,4-triazol-3yl]benzaldehyde
3-(3-ethoxyphenyl)-5-[2-(1-hydroxyethyl)phenyl]-1H-1,2,-4-triazole
5-(2-hydroxymethylphenyl)-3-(3-propargyloxyphenyl)-1H-1,2,4-triazole
5-(2-hydroxymethylphenyl)-3-(4-trifluoromethylphenyl)-1H-1,2,4-triazole 5-[2-(1-hydroxyethyl)-phenyl]-3-(3-methoxyphenyl)-1H-1,2,4-triazole
3-(4-fluorophenyl)-5-(2-hydroxymethylphenyl)-1H-1,2,4-triazole
5-(2-hydroxymethylphenyl)-3-(1,1'-bisphenyl-4-yl)-1H-1,2,4-triazole
2-[5-(1,1'-Bisphenyl-4-yl)-1H-1,2,4-triazol-3-yl]benzaldehyde
5-(2-hydroxymethylphenyl)-3-(4-methylphenyl)-1H-1,2,4-triazole
5-(2-hydroxymethylphenyl)-3-(3,4-methylenedioxyphenyl)-1H-1,2,4-triazole
5-(2-hydroxymethylphenyl)-3-(3,5-dimethoxyphenyl)-1H-1,2,4-triazole
5-(2-hydroxymethylphenyl)-3-(3,4-dimethoxyphenyl)-1H-1,2,4-triazole
2-[5-(3,5-dimethoxyphenyl)-1H-1,2,4-triazol-3-yl]benzaldehyde
5-(4-chloro-2-hydroxymethylphenyl)-3-(3-methoxyphenyl)-1H-1,2,4-triazole 5-(2-hydroxymethyl-4-methylphenyl)-3-(3-methoxyphenyl)-1H-1,2,4-triazole
5-(2-hydroxymethyl-6-methylphenyl)-3-(3-methoxyphenyl)-1H-1,2,4-triazole
5-(2-hydroxymethyl-4-methoxyphenyl)-3-(3-methoxyphenyl)-1H-1,2,4-triazole
3-methoxy-6-[5-(3-methoxyphenyl)-1H-1,2,4-triazol-3yl]benzaldehyde
5-(2-hydroxymethyl-4-methoxyphenyl)-3-(2-methylphenyl)-1H-1,2,4-triazole
5-(2-hydroxymethyl-4-chlorophenyl)-3-(2-methylphenyl)-1H-1,2,4-triazole
5-[2-(1-hydroxyethyl)-4-methoxyphenyl]-3-(2-methylphenyl)-1H-1,2,4-triazole
5-(2-hydroxymethylphenyl)-3-(2,4-dimethylphenyl)-1H-1,2,4-triazole
5-(2-hydroxymethylphenyl)-3-(2,4-dichlorophenyl)-1H-1,2,4-triazole
5-(2-methoxymethylphenyl)-3-(3-methoxyphenyl)-1H-1,2,4-triazole
5-(2-methoxymethylphenyl)-3-(3-ethoxyphenyl)-1H-1,2,4-triazole

EXAMPLE 5

A vial for injectable use is prepared from

| | |
|---|---|
| 5-(2-hydroxymethylphenyl)-3-(3-methoxyphenyl)-1H-1,2,4-triazole | 20 mg |
| Benzyl alcohol | 100 mg |
| Castor oil q.s. to | 2 ml |

EXAMPLE 6

A vial for injectable use is prepared from

| | |
|---|---|
| 2-[5-(3-methoxyphenyl)-1H-1,2,4-triazol-3-yl]benzaldehyde | 30 mg |
| Benzyl benzoate | 250 mg |
| Sesame oil q.s. to | 2 ml |

EXAMPLE 7

A capsule is prepared from

| | |
|---|---|
| 5-(2-hydroxymethylphenyl)-3-(3-methoxyphenyl)-1H-1,2,4-triazole | 150 mg |
| Stearic acid | 30 mg |
| Lactose | 120 mg |

We claim:

1. A method for preventing reproduction in a warm-blooded animal which comprises administering to the animal a dosage from about 0.8 to about 50 mg/Kg of body weight of a compound of the formula

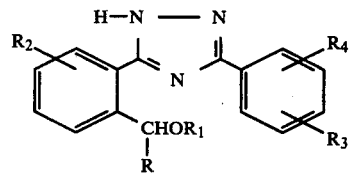

wherein R represents hydrogen or methyl, $R_1$ represents hydrogen or ($C_1$-$C_4$) alkyl, or R and $R_1$ taken together represent a further bond between the carbon and the oxygen atom, $R_2$ represents hydrogen, chloro, fluoro, bromo, ($C_1$-$C_4$) alkyl or ($C_1$-$C_4$) alkoxy, $R_3$ represents ($C_1$-$C_4$) alkyl, ($C_1$-$C_4$) alkoxy, allyloxy, propargyloxy, trifluoromethyl, phenyl, chloro, fluoro, bromo or dimethylamino and $R_4$ represents hydrogen, chloro, fluoro, bromo, ($C_1$-$C_4$) alkyl or ($C_1$-$C_4$) alkxoy or $R_3$ and $R_4$ taken together represent a methylenedioxy group.

* * * * *

UNITED STATES PATENT AND TRADEMARK OFFICE
CERTIFICATE OF CORRECTION

PATENT NO. : 4,370,337

DATED : January 25, 1983

INVENTOR(S) : P. Consonni, et al.

It is certified that error appears in the above-identified patent and that said Letters Patent are hereby corrected as shown below:

On the cover page, the patent reads "Filed: Jul. 16, 1980" and should read --Filed: July. 16, 1981--.

At column 4, line 15, the patent reads ">10>20" and should read -->10<20--.

At column 4, line 28, the patent reads "incorporated" and should read --incorporable--.

At column 6, lines 11-12, the patent reads "chromtography" and should read --chromatography--.

At column 8, line 37, the patent reads "$(C_1-C_4)$alkxoy" and should read --$(C_1-C_4)$alkoxy--.

Signed and Sealed this

Twenty-sixth Day of January, 1988

Attest:

DONALD J. QUIGG

*Attesting Officer*  *Commissioner of Patents and Trademarks*